Figure 1:
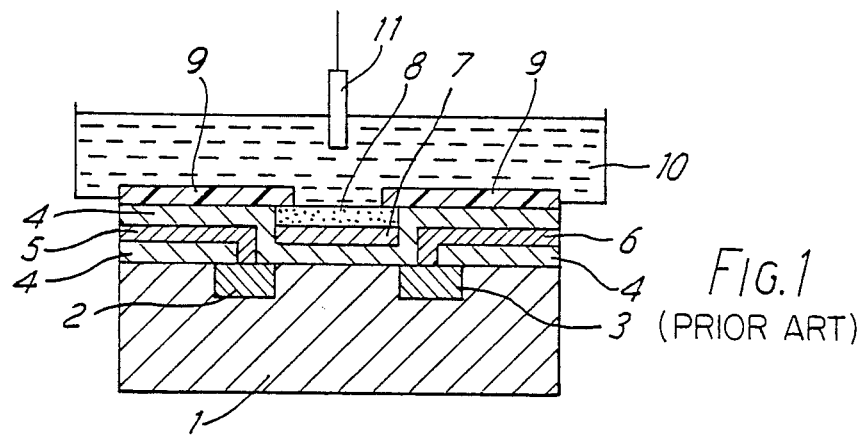

United States Patent [19]

Eddowes

[11] Patent Number: 4,839,000

[45] Date of Patent: Jun. 13, 1989

[54] BUFFER COMPENSATION IN ENZYME-MODIFIED ION SENSITIVE DEVICES

[75] Inventor: Mark J. Eddowes, Uxbridge, England

[73] Assignee: Thorn EMI plc, London, United Kingdom

[21] Appl. No.: 933,246

[22] Filed: Nov. 21, 1986

[30] Foreign Application Priority Data

Nov. 22, 1985 [GB] United Kingdom ............... 8528794

[51] Int. Cl.$^4$ ........................................... G01N 27/46
[52] U.S. Cl. .................................. 204/1 T; 204/403; 204/405; 204/406; 204/416
[58] Field of Search ............... 204/1 T, 403, 405–406, 204/416

[56] References Cited

U.S. PATENT DOCUMENTS

| 3,878,059 | 4/1975 | Wechter et al. | 204/405 |
| 4,230,554 | 10/1980 | Blanke | 204/405 |
| 4,305,802 | 12/1981 | Koshiishi | 204/195 |
| 4,312,715 | 1/1982 | Albery et al. | 204/405 |

FOREIGN PATENT DOCUMENTS

1529743 10/1978 United Kingdom.

OTHER PUBLICATIONS

"Field Effect Transistor Sensitive to Penicillin", by Steve Caras & J. Janata, Anal. Chem. 1980, 52, pp. 1935–1937.

"Chemical Sensors", by Y. Miyahara, et al., Analytical Chemistry Symposia Series, vol. 17 (1983), pp. 501–506.

"Response of an Enzyme-Modified pH-Sensitive Ion Selective Device; Consideration of the Influence of the Buffering Capacity of the Analyte Solution", by M. j. Eddowes, Sensors and Actuators 7 (1985), pp. 97–115.

"Response of an Enzyme-Modified pH-Sensitive Ion-Selective Device; Experimental Study of a Glucose Oxidase-Modified Ion-Sensitive Field Effect Transistor in Buffered and Unbuffered Aqueous Solution", by M. J. Eddowes, et al., Sensors and Actuators 7 (1985), pp. 233–244.

"pH-Based Enzyme Potentiometric Sensors. Part 1. Theory", by Steve D. Caras and J. Janata, Anal. Chem. 57 (1985), pp. 1917–1925.

"Chemical-sensitive field-effect transistors", by A. Sibbald, IEE Proceedings, vol. 130 Pt. 1, No. 5, Oct. 1983, pp. 233–244.

"Chemically sensitive field-effect transistors", by J. Janata and Stanley D. Moss, S. D., Biomedial Engineering, Jul. 1976, pp. 241–245.

"Coulometric Flow Analyzer for Use with Immobilized Enzyme Reactors", by Robert Adams and Peter Carr, Analytical Chemistry, vol. 50, No. 7, 1978 pp. 944–950.

"An ISFET-Based Microlitre Titrator: Integration of a Chemical Sensor-Actuator System," Van Der Schoot et al., based on paper presented at Third Internat'l. Conference on Solid-State Sensors and Actuators, Philadelphia, PA, Jun. 11–14, 1985, pp. 11–22.

*Primary Examiner*—John F. Niebling
*Assistant Examiner*—Ben C. Hsing
*Attorney, Agent, or Firm*—Fleit, Jacobson, Cohn, Price, Holman & Stern

[57] ABSTRACT

A system suitable for determining the concentration of an enzyme's substrate in a solution 21 containing a buffer comprises two ion-sensitive devices 22, 23, such as ISFETS, in contact with the solution, one of the devices 23, e.g. an ENFET, having a layer 24 containing an enzyme, the enzyme producing ions from its substrate, and the system comparing the responses of the two devices and providing a control signal to consume ions as they are generated at the ENFET, or to produce an equal concentration of ions at the other device, such that the concentrations sensed by each are equal. The signal gives an indication of the concentration of the substrate. Other ion-sensitive devices may be used. The concentration of other substances can be determined, for example a device with an enzyme's substrate can be used for detecting the concentration of an enzyme.

15 Claims, 4 Drawing Sheets

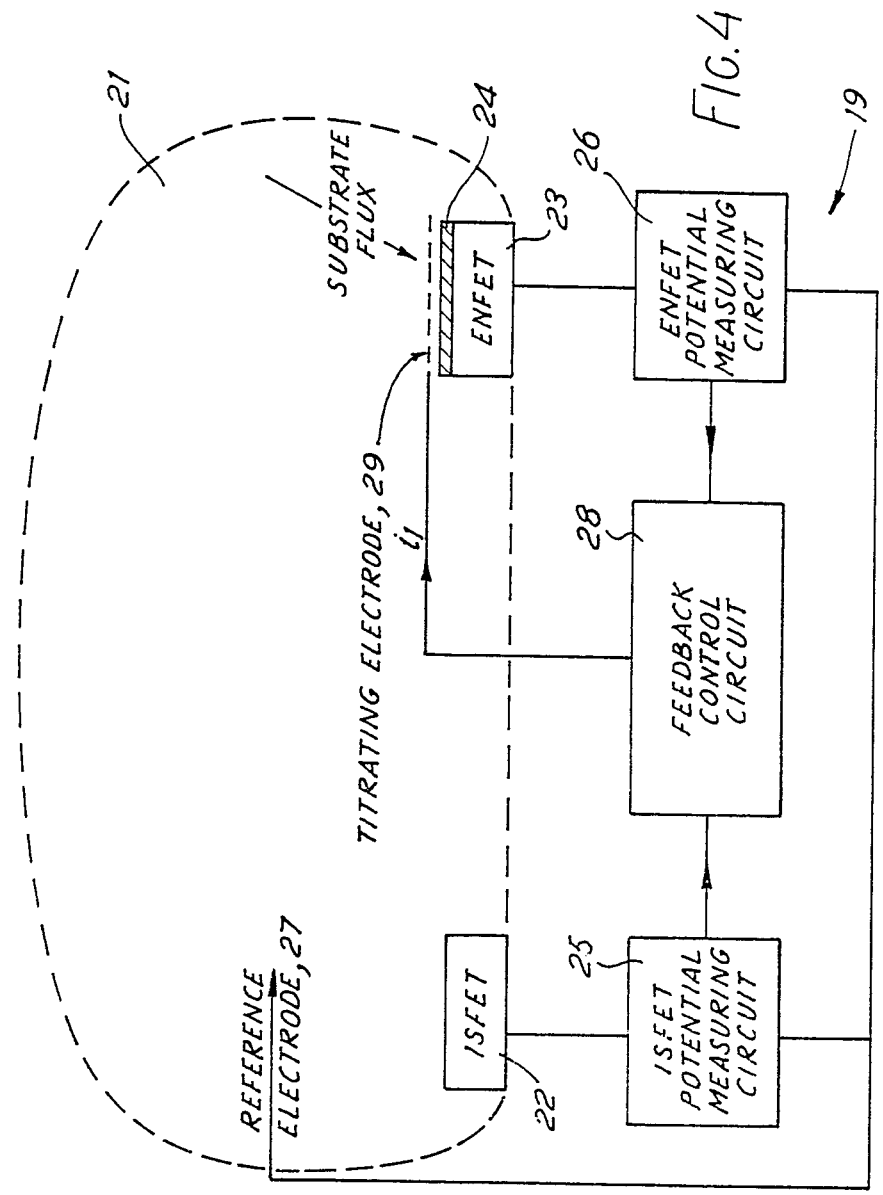

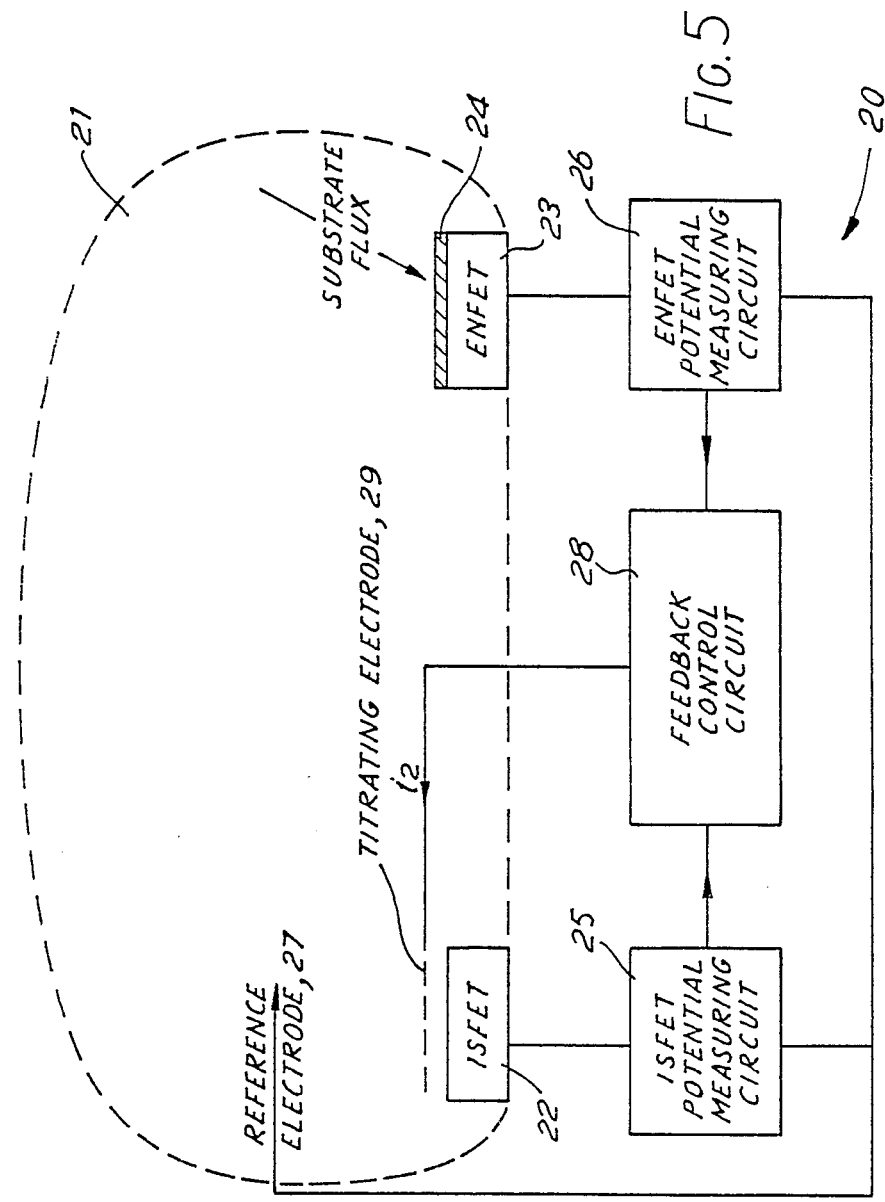

BUFFER COMPENSATION IN ENZYME-MODIFIED ION SENSITIVE DEVICES

This invention is related to a system and method for measuring the concentration of a substance in a solution, useful when the solution contains a buffer. It also relates to a device which may be used in such a system. The invention applies to the use of ion-sensitive devices and in particular to enzyme-modified ion sensitive devices.

The structure and operation of the ENFET (enzyme-modified ion sensitive field effect transistor) is well known (see for example Caras, S. and Janata, J., Anal. Chem. 1980, 52, pp. 1935–1937 and Miyahara, Y. et al., Analytical Chemistry Symposis Series, 17 (1983)) and may be summarized as follows:

An ENFET (shown schematically in FIG. 1) is an ion-sensitive device consisting of a semiconductor substrate 1, with source and drain regions 2 and 3 respectively diffused into it. Metal conductors 5 and 6 provide electrical connections to the source and drain. An ion-sensitive layer 7 is insulated from the channel between the source and drain by insulating material 4. This layer is overlaid by a thin film layer or membrane 8 and the device is encapsulated by layer 9. The ENFET may be placed in contact with a solution 10 which is to be analysed. If a reference electrode 11 is placed in the solution, the electrical potential across the reference electrode/solution interface is constant. If the membrane 8 has an enzyme immobilized in it, the device can detect the concentration of the enzyme's substrate in the solution with which the enzyme may react, by virtue of the fact that the enzyme will produce, for example, a certain number of ions to which the ion-selective layer is sensitive, for each mole of the substrate it reacts with and the potential across the ion-selective layer/membrane interface varies accordingly. Conversely, the substrate upon which an enzyme will act may be immobilized in layer 8 and the concentration of the corresponding enzyme can then be detected. Such a device is described in fuller detail in Patent No. GB 1529743.

Taking as an example the case when an enzyme acts on its substrate to give an acid,

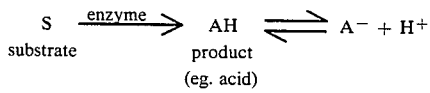

i.e. the hydrogen ($H^+$) ions may be detected by a pH sensitive layer.

It is known to take two ISFETs (see Caras and Janata), one with and one without an enzyme layer, and compare the two responses by placing them in the same solution and connecting them in the differential mode. Since the device having the enzyme layer will, for example as in the above case, generate protons in the presence of the enzyme's substrate and the other device will not, a comparison of their responses reflects the number of protons generated from the substrate. This differential mode of measurement will automatically compensate to some extent for changes in ambient solution conditions since such changes affect the enzyme-modified and reference ISFETs equally, provided that the temperature and pH characteristics of each device are the same.

Problems arise however when the above arrangements are used with solutions which have buffering capacity, such as clinical and other samples, (see for example Eddowes M.J., Sensors and Actuators 7(1985) 97–115, Eddowes et al., Sensors and Actuators 7 (1985) 233–244 and Caras et al. Anal. Chem. 57(1985) 1917–1925). In this case, the sensitivity of the device to the enzyme's substrate will be reduced by an indeterminate amount. If, for example, an enzyme acts to produce a certain number of moles of $H^+$ ions per mole of its substrate, this amount of $H^+$ is not detected by the device because the buffer reacts immediately with some of the $H^+$ ions. Furthermore, in the differential mode, the measured potential is a function of the difference between the logarithms of the bulk solution and surface pH values such that the differential potential is also a function of bulk solution pH. Hence the detected pH does not change in simple relation to the enzyme's substrate concentration.

In the prior art, solutions of defined buffer capacity and pH have been analysed and it has been shown that ENFETs produce a change in pH great enough to be measured by conventional methods. In this case it is possible to calibrate the response of the device for these specific conditions, but the response is of complicated form and varies with buffer concentration and bulk solution pH.

It is an object of the invention to alleviate some of the disadvantages, as described above, of the prior art.

According to the invention there is provided a system suitable for measuring the concentration of a first substance in a solution which contains ions, the system comprising two ion sensitive devices, each device incorporating means sensitive to said ions and one of said devices further incorporating a second substance which causes additional said ions to be produced when said second substance is exposed to said first substance and each device having an output response related to a concentration of ions sensed by the ion-sensitive means, said output responses having a predetermined relationship to each other whenever the concentrations of said ions detected by the two devices are substantially equal; and an electrical control circuit for controlling the concentration of ions detected by one or the other of said devices, thereby enabling their responses to attain said predetermined relationship, and for generating an electrical signal which is indicative of said concentration of said first substance whenever said predetermined relationship is attained.

The second substance could be an enzyme suitable for use in the measurement of the concentration of a corresponding enzyme substrate, or vice versa. The ion sensitive devices may be ISFETs an (ENFET"), said one device being an enzyme - modified ISFET.

In a particular embodiment of a system, the electrical control circuit includes a comparison circuit for measuring a difference between the two responses to produce a comparison signal, the comparison signal being used to effect the control of ion concentration.

The system may include a titrating electrode and a counter electrode wherein the comparison signal is used to control a current via the two electrodes thereby to effect the control of ion concentration.

The current passed may create a change in ion concentration to essentially match or cancel the change in ion concentration produced by the action of the enzyme.

The ions generated are preferably H+ ions, in which case the ion-sensitive devices, for example an ENFET and an ISFET, are pH sensitive, the diffusional flux of the substrate generates a local porton concentration change in the enzyme layer, and the pH values at the ion sensitive layers of the ENFET and ISFET are maintained essentially equal.

When the devices used are an ENFET and an unmodified ISFET, the titrating electrode may be at the gate of the ENFET and may surround the gate of the ENFET. The titrating current may be passed to keep the pH value at the ion-sensitive layer of the ENFET essentially constant. Alternatively, the titrating electrode may be at the gate of the ISFET, in which case the titrating current is passed to create an ion or pH change equal to that caused by enzyme action at the ENFET, so that the potential responses of the two devices are matched.

In each of the above cases, the current is related to the change in ion concentration or pH brought about by enzyme action.

The potential response and hence ion concentration (or pH value) at the ion-sensitive layer of the devices may be measured by circuit means such as that described in "Chemical-sensitive field effect transistors" (Sibbald, A., IEE Proceedings, Vol. 130., Pt. 1, No. 5, Oct. 1983) with reference to FIG. 6 of this paper. That is, for each device the source-drain current (which is dependent upon the potential across the conducting channel) may be measured, or alternatively the source-drain current may be maintained at a constant value by means of a simple feedback loop, so that changes in potential across the device may be measured directly.

According to a further aspect of the invention there is provided an ion-sensitive device having a titrating electrode.

According to another aspect of the invention there is provided a method suitable for determining the concentration of a first substance in a solution containing ions, the method including generating additional said ions by the interaction of said first substance and a second substance to produce a change in ion concentration at a test location, the number of ions generated being related to the concentration of said first substance; comparing the concentration of ions at a reference location with that at the test location and modifying the ion concentration at one of said locations to cause substantial equality of ion concentration at said locations, the extent of the modification being related to the concentration of said first substance in the solution.

Figure 2A:
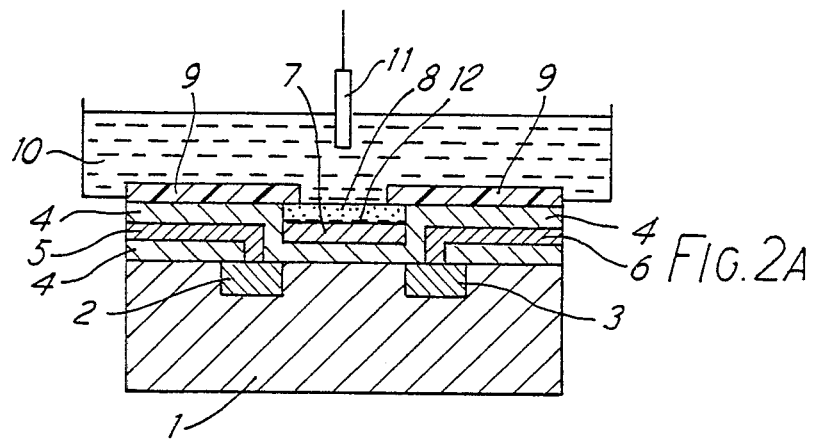
Figure 2B:
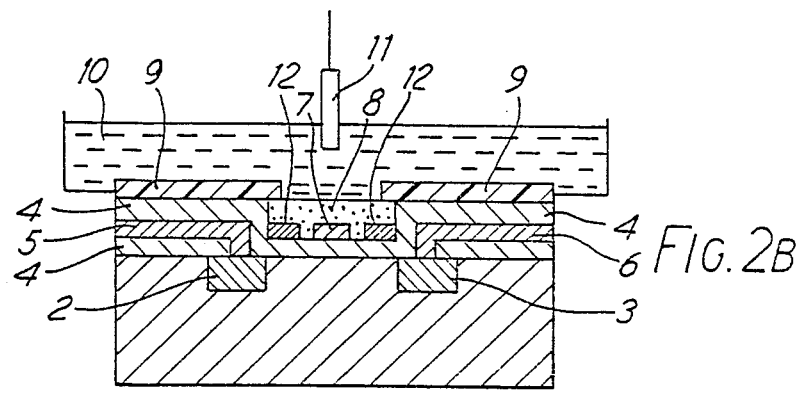
Figure 3:
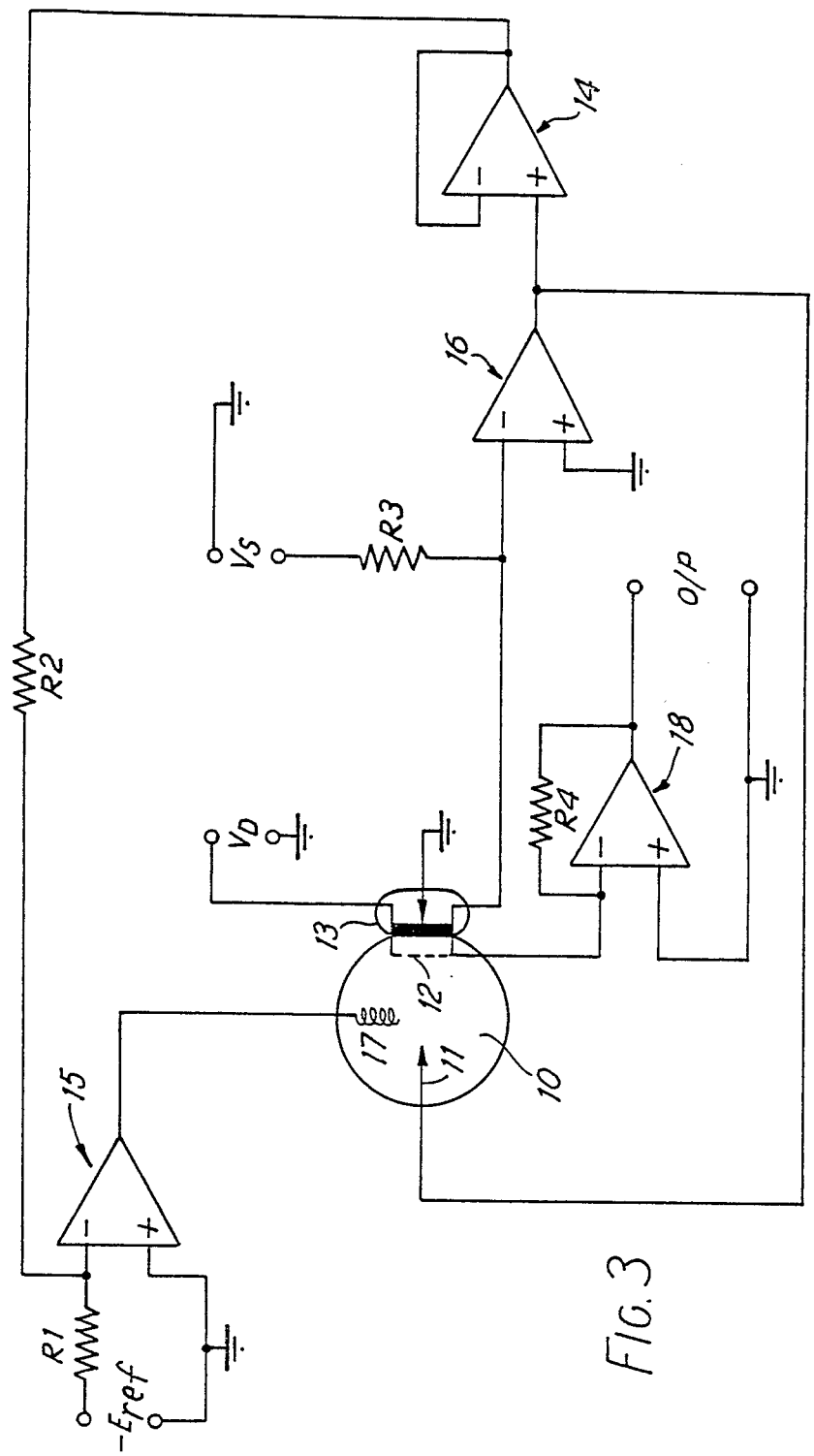

In order that the invention may be clearly understood and readily carried into effect, it will be described by way of example with reference to the accompanying drawings of which:

FIG. 1 is a schematic representation of an enzyme-modified ion-sensitive field effect transistor (ENFET) as known in the prior art and as described earlier, FIG. 2A represents a possible construction of an ENFET having a titrating electrode between the enzymes; and ion-sensitive layers, FIG. 2B represents a possible construction of an ENFET having a titrating electrode surrounding the gate, FIG. 3 shows a titrating circuit, FIG. 4 schematically represents a circuit for compensation for enzyme-generated ions, and FIG. 5 schematically represents a circuit which generates a change in ion concentration to match that produced by an enzyme.

FIG. 2A represents a possible construction of an ENFET with a titrating electrode, for use in the invention. The construction is similar to the known ENFET shown in FIG. 1, in that it is built on a substrate 1, and an ion sensitive layer 7 is provided over an insulating layer 4. However, adjacent to the enzyme layer 8, there is a titrating electrode 12. The electrode may be in the form of a suspended mesh. Alternatively, the titrating electrode 12 may be adjacent and surrounding the ion-sensitive gate material 7 of the FET as shown in FIG. 2B. (An ISFET with an enzyme substrate layer may also have a titrating electrode and be of similar construction to the ENFET device of FIG. 2A.)

Considering the case when the enzyme acts on the substrate to produce protons, when a current is passed through the titrating electrode, electrons are provided which can consume protons generated within the enzyme layer, i.e.

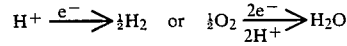

By use of a feedback circuit, the concentration of H+ ions can be maintained by consuming H+ ions generated due to the enzyme action before they can reach the bulk solution or the ion-(or pH-) sensitive layer.

It is also possible to supply a current manually to compensate for generated ions.

Setting out some theory,
if at time t=O,
there are
    x moles of H+ present,
    y moles of B− present,
    n moles of substrate,
    and m moles of BH (buffer) in known equilibrium and
      if n moles of product (=A−/H+) were then to be generated,
x+n moles of H+ would then be present.
But H+ may react with B− to form z moles of BH.
(The presence of H+ perturbs the original equilibrium.)
Then there would be
(x+n−z) moles of H+ (which can be registered as a pH change by an enzyme-modified ISFET),
(y−z) moles of B−
and (m +z) moles of BH.
(In the above discussion, A and B are used to represent appropriate chemical symbols.)

The host ISFET device of the ENFET senses [H+] via a change in potential. If this potential were to act in a feedback loop containing the titrating electrode, the [H+] as reflected by the potential could be kept constant. In order to maintain the [H+] constant, a titrating current equivalent to the perturbation produced by the enzyme (i.e. n moles of electrons) must be supplied. This would restore the original pH/buffer balance. (This is the feedback loop mode, and in fact the system is never shifted out of equilibrium.)

FIG. 3 represents a "titrating" circuit considered to be suitable for implementing the invention. Device 13 is preferably an enzyme-modified pH-sensitive FET (pH-ENFET), having a titrating electrode 12 associated with it. Device 13 is placed in contact with a solution 10 (the analyte), the solution contained the enzyme's substrate, the concentration of which it is desired to determine. A pH-sensitive FET (pH-ISFET) (not shown in FIG. 3), which is similar in all essential respects to the pH-ENFET shown except that it has no enzyme layer, is placed in contact with the same solution. $E_{ref}$, the gate potential of the pH-ISFET, may be applied as shown in FIG. 3.

In FIG. 3, if R1=R2, the output of the voltage follower 14 is $E_{ref}$ (because of the virtual earth at the negative input of operational amplifier 15). Since operational amplifier 14 is a voltage follower, the output of operational amplifier 16 is also $E_{ref}$.

Considering the pH-ENFET, if $V_{sub}$ is the potential of the semiconductor substrate and $E_i$ is the potential at the surface of the insulator adjacent to the ion-(or pH-) sensitive layer, then to keep the source-drain current $i_D$ constant, the potential across the conducting channel $(V_{sub} - E_i)$ must be kept constant.

RE is the potential at the reference electrode 11 and $(V_{sub} - RE) = (V_s - E_i) = \Delta E_m$ can be measured. $i_D$ is set using $V_s$ and $V_D$ as shown. $V_D$ is the drain voltage.

The output of 16 is fed to the reference electrode, so RE and $E_{ref}$ must be set equal. The circuit will measure the difference between RE and the substrate voltage for the pH-ENFET.

$$V_{sub} - RE = C + \Delta E_m$$

$$\Delta E_m = \frac{RT}{F} \ln [H^+]_{enz}$$

where $\Delta E_m$ is the potential due to hydrogen ions, R is the gas constant, T is the temperature, F is the Faraday constant and $[H^+]_{enz}$ is the concentration of H+ ions at the surface of the ion-sensitive layer in the ENFET. For the reference pH-ISFET, $$\overline{E_{ref}} = \overline{(V_{sub} - RE)} = C' + \overline{\Delta E_m} \quad \text{(bars denote reference pH-}ISFET\text{)}$$

where $\overline{\Delta E_m} = \frac{RT}{F} \ln [H^+]_\infty$, $[H^+]_\infty$ is the concentration of H+ ions in the bulk solution, indicated by the pH of the bulk solution which may be measured.

The constants C and C' vary depending on the situation and the calibration may be adjusted so that they are equal or they may be trimmed to zero.

The following is believed to be the explanation of the circuit operation:

In constructing the circuitl, due account has to be taken of the specific devices. It is through to be preferable that for optimum operation the titrating part of the circuit should be allowed to float with respect to the rest of the circuit and the earths of the two operational amplifiers 15 and 18 should be common, but different from the other earths in the circuit which should be common to each other.

If $V_{sub}$-RE$\neq E_{ref}$ (due to the enzyme altering the local hydrogen ion concentration from the hydrogen ion concentration in the bulk solution), the potential at the negative input of operational amplifier 15 is not a virtual earth. Amplifier 15 therefore outputs a current which flows through the counter electrode 17. (The counter electrode may be made from a noble metal e.g. platinum gauze). The current cannot flow to the ENFET itself (since the ENFET gate is an insulator) and it cannot flow to the reference electrode since this is connected to the input of operational amplifier 14. The current therefore flows through the titrating electrode to a virtual earth input of operational amplifier 18 (which is a current-voltage converter) and through resistor R4 to the output o/p of 18. The voltage output of amplifier 18 is proportional to the titrating current and hence to the concentration of substrate upon which the enzyme acts.

In the circuit shown, in order to measure the titrating current it is also possible to connect the titrating electrode 12, rather than the auxiliary counter electrode 17, to the output of operational amplifier 15 and to connect the counter electrode to the input of operational amplifier 18.

It is also possible to remove the resistor R4, operational amplifier 18 arrangement altogether and instead to connect titrating electrode 12 (or in the case described in the immediately preceding paragraph, counter electrode 17) straight to earth. Measurement of the voltage across a resistance connected, for example, between the output of 15 and counter electrode 17 (or titrating electrode 12, as appropriate) would then give an indication of the titrating current.

If protons are generated from the substrate due to enzyme action, they must be consumed at the titrating electrode to make $V_{sub}$ - RE = $E_{ref}$. With suitable positioning of the titrating electrode, the problems associated with the prior art of the protons diffusing away, reacting again to form the substrate or reacting with buffer, prior to detection, can be compensated for.

In a second embodiment of a titrating circuit the device 13 in FIG. 3 is a "dummy" pH-ENFET, a pH-ISFET which has a titrating electrode associated with it. In this device, the pH-sensitive gate material may be covered not with an enzyme layer but with a suitably porous electrode material (the titrating electrode) as in the pH-ENFET device described earlier. Alternatively, the titrating electrode may be adjacent and surrounding the ion-sensitive gate material. By means of the titrating electrode, protons may be either generated or destroyed by passing a current via an auxiliary electrode (the counter electrode 17) in the solution.

If $E_{ref}$ in this case is provided by a conventional pH-ENFET, the potential response of the "dummy" pH-ENFET may be made to match that of the pH-ENFET by virtue of the controlled current via the titrating electrode, in the feedback circuit. In such conditions, the current flowing through the titrating electrode at the "dummy" ENFET gate will be equivalent to the diffusional flux of the analyte to the conventional pH-ENFET gate. This is because the rate at which H+ ions are produced by the enzyme at the conventional pH-ENFET gate depends on the diffusional flux of the analyte to the conventional pH-ENFET gate. The effect of the buffering capacity of the analyte solution on H+ ions produced by the dummy and real ENFETS, and hence on the potential responses of the two devices, will be equivalent since they are both in contact with the same solution. Hence whilst the potential responses will vary with buffer capacity, the diffusional flux and current will always match and the current may therefore be used to determine the concentration of the enzyme's substrate in the bulk solution.

In the present invention, the ISFET and ENFET or other ion-sensitive devices are not necessarily pH-sensitive as described in the examples above. As with conventional ISFETs, the devices can be made sensitive to other types of ion by using different ion-sensitive layers.

If the ions which are generated by the action of the enzymes on the substrate are of valencies other than one (as for hydrogen ions), this must be taken into account when relating the current in the feedback loop to the ion concentration.

FIGS. 4 and 5 schematically represent different embodiments (19 and 20 respectively) of circuits for determining the concentration of the enzyme's substrate in an analyte solution 21 containing a buffer. Each circuit comprises an ISFET 22 and an ENFET 23 in contact with the solution, the ENFET and ISFET being similar in all essential respects except that the ENFET further includes an enzyme layer 24 containing an enzyme which acts on the substrate to generate ions to which the ion-sensitive layers in the ENFET and ISFET are selective. ISFET potential measuring circuit 25 measures the potential between the reference electrode 27 and the semiconductor substrate of the ISFET, and ENFET potential measuring circuit 26 measures the potential between the reference electrode and the semiconductor substrate of the ENFET. Feedback control circuit 28 compares these potentials and provides a current proportional to the difference. This titrating current flows through the titrating electrode 29 which, in the ciricuit 19 of FIG. 4 is associated with the ENFET, and in the circuit 20 shown in FIG. 5 is associated with the ISFET. In circuit 19, the titrating current $i_1$, compensates for enzyme-generated ions and in circuit 20, the titrating current $i_2$ generates an ion concentration matching that of the ENFET. In each case the titrating current is essentially equivalent to the diffusional flux of the enzyme's substrate to the ENFET and hence is proportional to the concentration of the enzyme's substrate in the analyte solution.

The invention is particularly useful when the devices are pH-sensitive. Also, the materials used for the insulating layers in ISFETs are often pH-sensitive and it is not necessary to include a further pH-selective membrane. It should be noted than an ENFET is a particular type of ion-sensitive field-effect transistor, and falls under the general classification of "ISFET".

If the enzyme's substrate rather than the enzyme is immobilised in the enzyme layer of the ENFET, the invention can be used to detect the concentration of the enzyme in a solution, rather than the concentration of its substrate.

The invention also encompasses use of ion-sensitive devices other than ion sensitive FETs, for example ion-selective electrodes (ISEs), metal/metal oxide pH sensors, and other metal/metal salt ion sensors.

I claim:

1. A system for measuring the concentration of a first substance in a solution, the system comprising a first and a second ion-sensitive device, one of said devices including a second substance which causes ions to be produced when said second substance is exposed to said first substance, the number of ions produced being related to the concentration of said first substance, each device incorporating ion-sensitive means sensitive to said ions, whereby a concentration of said ions can be sensed by said ion-sensitive means; and
   an electrical control circuit for passing a current to control the concentration of said ions detected by one of said devices, so as to cause substantial equality of the concentration of said ions at said first and said second devices, the magnitude of said current being indicative of said concentration of said first substance.

2. A system according to claim 1 in which the said second substance is an enzyme and said first substance is a substrate for the enzyme.

3. A system according to claim 2 in which the ion-sensitive devices are ion-sensitive field effect transistors, said one of said devices being an enzyme-modified ion-sensitive field effect transistor.

4. A system according to claim 1 in which said first substance is an enzyme and said second substance is a substrate for the enzyme.

5. A system according to claim 1 in which the electrical control circuit includes a titrating electrode disposed adjacent said ion sensitive means of one of said devices.

6. A system according to claim 5 in which the titrating electrode is in the form of a suspended mesh.

7. A system according to claim 1 in which the devices are pH sensitive.

8. A system according to claim 1 including a titrating electrode adjacent the ion-sensitive means of one of said devices and a counter electrode wherein the current flows via the titrating electrode and counter electrode thereby to effect said control of ion concentration.

9. A system according to claim 1 wherein each device develops a potential related to the concentration of said ions, the magnitudes of said potentials having a predetermined relationship whenever the concentrations of said ions detected by said first and said second devices are substnatially equal and the electrical control circuit causes said substantial equality by substantially maintaining said predetermined relationship.

10. A system according to claim 9 arranged so that the potentials developed are substantially equal whenever the concentrations of said ions detectedby the two devices a re substantially equal.

11. A system for measuring the concentration of a first substancein a solution, the system comprising a first and a second ion-sensitive device, one of said devices including a second substance which causes ions to be produced when said second substance is exposed to said first substance, the number of ions produced being related to the concentration of said first substance, each device incorporating ion-sensitive means sensitive to said ions, each device having an output response related to a concentration of said ions sensed by its ion-sensitive means, the difference between the output responses having a predetermined value whenever the concentrations of said ions detected by said first and said second devices are substantially equal, and an electrical control circuit for passing a current to control the concentration of said ions detected by one of said devices, so as to substantially maintain said difference at said predetermined value, whereby the concentrations of said ions detected by said first and said second devices are maintained substantially equal and the magnitude of said current is proportional to the concentration of said first substance.

12. A system according to claim 11 in which the electrical control circuit includes a comparison circuit for measuring a difference between the two output responses to produce a comparison signal, the comparison signal being used to effect the control of ion concentration.

13. A system for measuring the concentration of an enzyme's substrate in a solution, the system comprising a first and a second ion-sensitive device, said first device including an enzyme which causes ions to be produced when the enzyme is exposed to the substrate, the number of ions produced being related to the concentration of the substrate, each device incorporating ion-sensitive means sensitive to said ions, whereby a concentration of said ions can be sensed by said ion-sensitive means; and an electrical control circuit for passing a current to control the concentration of said ions detected by one of said devices, so as to cause substantial equality of the concentration of said ions at said first and said second devices, the magnitude of said current being indicative of said concentration of the enzyme's substrate.

14. A system according to claim 13 wherein each device develops a potential related to the concentration of said ions, the magnitude of said potentials having a predetermined relationship whenever the concentrations of said ions detected by said first and said second devices are substantially equal and the electrical control circuit causes said substantial equality by substantially maintaining said predetermined relationship.

15. A method for determining the concentration of a first substance in a solution, the method including generating ions by the interaction of said first substance and a second substance to produce a change in ion concentration at a test location, the number of ions generated being related to the concentration of said first substance, comparing the concentration of ions at a reference location with that at the test location and passing a current to control the ion concentration at one of said locations to cause substantial equality of the ion concentration at said locations, the magnitude of the current being related to the concentration of said first substance in the solution.

* * * * *